US008080493B2

(12) United States Patent
Chubarova et al.

(10) Patent No.: US 8,080,493 B2
(45) Date of Patent: Dec. 20, 2011

(54) HETEROPOLYANIONS WITH LATE TRANSITION METAL ADDENDA ATOMS AND PROCESS FOR THEIR PREPARATION

(75) Inventors: Elena Vladimirovna Chubarova, Bremen (DE); Ulrich Kortz, Bremen (DE)

(73) Assignee: ExxonMobil Chemical Patents Inc., Houston, TX (US)

( * ) Notice: Subject to any disclaimer, the term of this patent is extended or adjusted under 35 U.S.C. 154(b) by 755 days.

(21) Appl. No.: 12/037,647

(22) Filed: Feb. 26, 2008

(65) Prior Publication Data

US 2009/0216052 A1  Aug. 27, 2009

(51) Int. Cl.
*B01J 23/40* (2006.01)
*B01J 23/02* (2006.01)
*C07C 51/16* (2006.01)

(52) U.S. Cl. ........ 502/326; 502/327; 502/339; 502/344; 562/546

(58) Field of Classification Search .................. None
See application file for complete search history.

(56) References Cited

U.S. PATENT DOCUMENTS 3,206,391 A * 9/1965 Gutberlet et al. ............. 208/110
2007/0287853 A1  12/2007 Smith

FOREIGN PATENT DOCUMENTS

EP       0 782 979     7/1997
WO    WO 2007/122431  11/2007

OTHER PUBLICATIONS

S.J. Angus-Dunne et al., A. Novel Heteropolymetalate Containing Palladium(s): Synthesis and Crystal Structure of K2Na6[Pd2W10O36]22H2O, 1994, J. Chem. Soc., Chem. Commun., pp. 523-524.
U. Lee et al., Synchrotron structure determination of an α-Keggin doubly PtIV-Substituted silicotungstate, (CH6N3)8[αSiPt2-W10O40]6H2O, Acta Crystallographica, Section C, 2003, C59, m152-m155.
U. Lee, Dipotassium Hexahydrogen-α-hexamolybdoplatinate(IV) Pentahydrate, K2[H6α-PtMo6O2]5H2O, Acta Crystallographica, Section C, 1994, C50, pp. 1657-1659.
U. Lee et al., "Anhydrous octaguanidinium hexatungstoplatinate(IV)", Acta Crystallographica, Section E, 2003, E59, m116-m118.
U. Lee et al., The Geometrical Isomerization on Acidification in hexamolybdoheteropoly Oxometalate. The Crystal Structure of (NH4)4.5[H3.5αPtMo6O24] 1.5 H2O, (NH4)4[H4β-PtMo6O24] 1.5H2O, and K3.5[H4.5αPtMo6O24]3H2O, Bulletin Korean Chemical Society, 1994, vol. 15, No. 1, pp. 37-45.
L.Bi et al., First Structurally Characterized Palladium(II)-Substituted Polyoxoanion: [Cs2Na(H2O)10Pd3(α-SbIIIW9O33)2]9-, Inorg. Chem., 2004, 43, pp. 3915-3920.
T.M. Anderson et al., A Late-Transition Metal Oxo Complex: K7Na9[O=PtIV(H2O)L2], L=[PW9O34]9-, Science, 2004, vol. 306, pp. 2074-2077.
L. Bi et al., The Palladium(II)-Substituted Tungstosilicate [Cs2K(H2O)uPd2WO(H2O)(A-α-SiW9O34)2]-, Inorg. Chem., 2004, 43, pp. 8367-8372.

L. Bi et al., "The Palladium(II)-Substituted, Lone Pair Containing Tungstoarsenates (III) [Na2(H2O)2PdWO(H2O)(αAsW9O33)2]10- and [Cs2Na(H2O)8Pd3(α-AsW9O33)2]9-", Eur. J. Inorg. Chem., 2005, pp. 3034-3041.
T.M. Anderson et al., A Palladium-Oxo Complex, Stabilization of This Proposed Catalytic Intermediate by an Encapsulating Polytungstate Ligand, J. Am. Chem. Soc., 2005, 127, pp. 11948-11949.
U. Lee et al., Facile Incorporation of Platinum(IV) into Polyoxometalate Frameworks: Preparation of [H2PtIVV9O28]5- and Characterization by 195Pt NMR Spectroscopy, Angew. Chem. Int. Ed. 2008, 47, pp. 793-796.
W.H. Knoth et al., "Heteropolyanions of the Types M3(W9PO34)212- and MM'M"(W9PO34)212: Novel Coordination of Nitrate and Nitrite", Am. Chem. Soc., Inorg. Chem., 1986, 25, pp. 1577-1584.
C.M. Tourne, "Chiral Polytungstometalates [WM3(H2O)2(XW9O34)w]12-(X=M=Zn or CO) and their M-Substituted Derivatives. Syntheses, Chemical, Structural and Spectroscopic Study of some D.L. Sodium and Potassium Salts", J.Chem. Soc., Dalton Trans., 1991, Issue 1, pp. 143-155.
Polyoxometalate Chemistry: From Topology via Self-Assembly to Applications (Ed.: M.T. Pope, A. Muller), Kluwer, Dordrecht, The Netherlands, 2001.
R. Neumann et al., "Noble Metal (RuIII, PdII, PtII) Substituted "Sandwich" Type Polyoxometalates: Preparation, Characterization, and Catalytic Activity in Oxidations of Alkanes and Alkenes by Peroxides", Am. Chem. Soc., Inorg. Chem. 1995, 34, pp. 5753-5760.
R. Neumann et al. "Catalytic oxidation with hydrogen peroxide catalyzed by 'sandwich' type transition metal substituted polyoxometalates", Jrnl. of Molecular Catalysis A: Chemical, 117, 1997, pp. 169-183.
U. Schuchardt et al., "Cyclohexane oxidation continues to be a challenge", Applied Catalysis A: General, 211, 2001, pp. 1-17.
V. Kogan et al., "Preferential catalytic hydrogenation of aromatic compounds versus ketones with a palladium substituted polyoxometalate as pre-catalyst", J. Chem. 2002, 26, pp. 272-274. W. Adam et al., "Chiral Hydroperoxides as Oxygen Source in the Catalytic Stereoselective Epoxidation of Allylic Alcohols by Sandwich-Type Polyoxometalates: Control of Enantioselectivity through a Metal-Coordinated Template", J. Org. Chem., 2003, 68, pp. 8222-8231.
W. Adam et al., "A Highly Chemoselective, Diastereoselective, and Regioselective Epoxidation of Chiral Allylic Alcohols with Hydrogen Peroxide, Catalyzed by Sandwich-Type Polyoxometalates: Enhancement of Reactivity and Control of Selectivity by the Hydroxy Group through Metal-Alcoholate Bonding", J. Org. Chem., 2003, 68, pp. 1721-1728.
K. Lii et al., "Cs2Pd3(P2O7)2 and Cs2Pd3(As2O7)2: A 3D Palladium Phosphate with a Tunnel Structure and a 2D Palladium Arsenate Containing Strings of Palladium Atoms", Inorg. Chem., 2004, 43, pp. 2499-2502.
D. Orosel et al., PdAs2O6, the First Paramagnetic Palladium Oxide, Z. Anorg. Allg. Chem., 2006, 632, pp. 1131-1133.
D. Frerichs et al., "Uber das erste Oxopalladat-Arsenat: KMgePd(AsO4)3", Sect. B, Am. Jrnl. of Chem. Sciences, 1995, 50(6), pp. 867-870.

* cited by examiner

*Primary Examiner* — Paul A Zucker
(74) *Attorney, Agent, or Firm* — Catherine L. Bell (57) ABSTRACT

The invention relates to polyoxometalates represented by the formula $(A_n)^{m+} [M_{13}X_8R_qO_y]^{m-}$ or solvates thereof, wherein A represents a cation, n is the number of the cations, m is the charge of the polyanion, M represents a transition metal selected from Pd, Pt, Au, Rh, Ir and mixtures thereof, X represents a heteroatom selected from As, Sb, Bi, P, Si, Ge, B, Al, Ga, S, Se, Te and mixtures thereof, and y is the number of oxygen atoms ranging from 32 to 40, a process for their preparation and their use for the catalytic oxidation of organic molecules.

38 Claims, 2 Drawing Sheets

HETEROPOLYANIONS WITH LATE TRANSITION METAL ADDENDA ATOMS AND PROCESS FOR THEIR PREPARATION

FIELD OF THE INVENTION

This invention relates to new polyoxometalates (POMs) containing Pd—, Pt—, Rh—, Ir— and/or Au-addenda atoms, a process for their preparation and their use for the catalytic oxidation of organic molecules.

BACKGROUND OF THE INVENTION

POMs are a unique class of inorganic metal-oxygen clusters. They consist of a polyhedral cage structure or framework bearing a negative charge which is balanced by cations that are usually external to the cage, and may also contain centrally located heteroatom(s) surrounded by the cage framework. Generally, suitable heteroatoms include Group 13 to 16 elements such as phosphorus, antimony, silicon and boron. The framework of POMs comprises a plurality of metal atoms (addenda), which can be the same or different, bonded to oxygen atoms. Up to now the framework metal is substantially limited to a few elements including transition metals from Group 5 and Group 6 in their high oxidation states, e.g., tungsten (VI), molybdenum (VI), vanadium (V), niobium (V) and tantalum (V).

The first example in the POM family is the so-called Keggin anion $[XM_{12}O_{40}]^{3-}$ with X being a heteroatom selected from a wide variety of elements such as phosphorus, and M being a Group 5 or Group 6 metal such as Mo or W. These anions consist of an assembly of corner- and edge-shared $MO_6$ octahedra of the metals of Groups 5 or 6 around a central $XO_4$ tetrahedron.

In the past, there have been increasing efforts towards the decoration of polyoxoanions with various organic and/or transition metal complex moieties with the aim of generating new catalyst systems as well as functional materials with interesting optical, electronic and magnetic properties. In particular, transition metal-substituted polyoxometalates (TMSPs) have attracted continuously growing attention as they can be rationally modified on the molecular level including size, shape, charge density, acidity, redox states, stability, solubility, etc. In particular, POMs comprising transition metals of Groups 9 to 11 of the periodic table of the elements (e.g., Pd and Pt) are of interest because they are thermally and oxidatively stable and possess highly attractive catalytic properties.

For example, Angus-Dunne et al. describe the preparation of palladium-substituted sandwich-type POM $K_2Na_6$ $[Pd_2W_{10}O_{36}].22H_2O$ (see: J. Chem. Soc., Chem. Commun. 1994, pp. 523-524). This polyanion is composed of two $W_5O_{18}^{6-}$ moieties linked by two palladium(II) ions in square-planar environments.

Lee et al. disclose the structure of several platinum(IV)-substituted POMs, such as $(CH_6N_3)_8[\alpha\text{-SiPt}_2W_{10}O_{40}]$. $6H_2O$, a Keggin-type polyanion in which two addenda atoms are replaced by Pt atoms (Acta Crystallographica, Section C, 2003, C59, m152-m155), as well as $K_2[H_6\text{-}\alpha\text{-PtMo}_6O_{24}]$ $5H_2O$ (Acta Crystallographica, Section C, 1994, C50, pp. 1657-1659), $(CH_6N_3)_8[PtW_6O_{24}]$ (Acta Crystallographica, Section E, 2003, E59, m116-m118), $(NH_4)_{4.5}[H_{3.5}\text{-}\alpha\text{-}PtMo_6O_{24}].1.5H_2O$, $(NH_4)_4[H_4\text{-}\beta\text{-PtMo}_6O_{24}].1.5H_2O$ and $K_{3.5}[H_{4.5}\text{-}\alpha\text{-PtMo}_6O_{24}].3H_2O$ (Bulletin of the Korean Chemical Society 1994, 15, pp. 37-45), which all have the so-called Anderson-Evans structure.

Kortz et al. report on the palladium(II)-substituted, dimeric, lone pair containing polyanion $[Cs_2Na(H_2O)_{10}Pd_3(\alpha\text{-SbW}_9O_{33})_2]^{9-}$ (Inorg. Chem. 2004, 43, pp. 3915-3920). This polyanion was synthesized by reacting $Pd(CH_3COO)_2$ with $[\alpha\text{-SbW}_9O_{33}]^{9-}$ in aqueous acidic medium. The square-planar palladium(II) ions are located in the central belt of the sandwich-type structure connecting two $(\alpha\text{-SbW}_9O_{33})$ Keggin moieties via bonding to oxygen atoms of the $WO_6$ octahedra.

Hill et al., Science 2004, 306, pp. 2074-2077, disclose the synthesis of the Pt (IV)-containing compound $K_7Na_9[Pt(O)(H_2O)(PW_9O_{34})_2].21.5H_2O$. The polyanion $[Pt(O)(H_2O)(PW_9O_{34})_2]^{16-}$ is composed of two $(A\text{-}\alpha\text{-PW}_9O_{34})$ Keggin units linked by an octahedral platinum(IV) center with terminal oxo and water ligands. Attempts to reproduce this complex proved unsuccessful.

Kortz et al., Inorg. Chem. 2004, 43, pp. 8367-8372, describe the synthesis of a palladium(II)-substituted tungstosilicate, $[Cs_2K(H_2O)_7Pd_2WO(H_2O)(A\text{-}\alpha\text{-SiW}_9O_{34})_2]^{9-}$. This polyanion was synthesized by reacting $Pd(CH_3COO)_2$ with $[A\text{-}\alpha\text{-SiW}_9O_{34}]^{10-}$ in aqueous acidic medium. It is composed of two $(A\text{-}\alpha\text{-SiW}_9O_{34})$ Keggin moieties which are linked via a central belt consisting of a $\{WO(H_2O)\}^{4+}$ group, two Pd(II) centers, one potassium ion and two cesium ions. The palladium(II) ions exhibit square-planar coordination geometry as they are only ligated to four oxo groups of the polyanion backbone. The potassium and cesium ions are also coordinated by terminal water molecules.

Moreover, Kortz et al. report on the palladium(II)-substituted, lone pair containing polyanion $[Cs_2Na(H_2O)_8Pd_3(\alpha\text{-AsW}_9O_{33})_2]^{9-}$ (Eur. J. Inorg. Chem. 2005, pp. 3034-3041). This polyanion was synthesized by reacting $PdCl_2$ with $[\alpha\text{-AsW}_9O_{33}]^{9-}$ in aqueous acidic medium. The square-planar palladium(II) ions are located in the central belt of the sandwich-type structure connecting two $(\alpha\text{-AsW}_9O_{33})$ Keggin moieties via bonding to oxygen atoms of the $WO_6$ octahedra. This polyanion can be considered as the As-analogue of the above mentioned $[Cs_2Na(H_2O)_{10}Pd_3(\alpha\text{-SbW}_9O_{33})_2]^{9-}$.

Kortz et al. also report on the palladium(II)-substituted, lone pair containing polyanion $[Na_2(H_2O)_2PdWO(H_2O)(\alpha\text{-AsW}_9O_{33})_2]^{10-}$ (Eur. J. Inorg. Chem. 2005, pp. 3034-3041). This polyanion was synthesized by reacting $PdCl_2$ with $[AS_2W_{19}O_{67}(H_2O)]^{14-}$ in aqueous acidic medium. It is composed of two $(\alpha\text{-AsW}_9O_{33})$ Keggin moieties which are linked via a central belt consisting of a $\{WO(H_2O)\}^{4+}$ group, a square-planar Pd(II) center and two sodium ions. One of the two sodium ions in the central belt is located in an addenda atom position, which appears to decrease the stability of this polyanion in solution.

Recently, Hill et al. describe the preparation of a Pd(IV)-oxo compound, $K_{10}Na_3[Pd^{IV}(O)(OH)WO(OH_2)(PW_9O_{34})_2]$, by reacting $PdSO_4$ with $[A\text{-}\alpha\text{-PW}_9O_{34}]^{9-}$ yielding $[Pd^{II}_3(PW_9O_{34})_2]^{12-}$ which undergoes rapid loss of Pd(II) to form $[PD^{II}WO(OH_2)(PW_9O_{34})_2]^{12-}$ and oxidation of this compound resulted in the Pd(IV)-oxo complex (Hill et al., J. Am. Chem. Soc. 2005, 127, pp. 11948-11949). This polyanion is composed of two $(A\text{-}\alpha\text{-PW}_9O_{34})$ Keggin moieties which are linked via a central belt consisting of a $\{WO(H_2O)\}^{4+}$ group and a $\{PdO(OH)\}^+$ group. The tungsten center in the belt has an internal oxo ligand and an external water ligand, whereas the Pd center has an internal oxo and an external hydroxy ligand.

Recently, Kortz et al. report on the Pt(IV)-containing polyvanadate $[H_2Pt^{IV}V_9O_{28}]^{5-}$ which is prepared by a one-pot reaction of $Na_2[Pt(OH)_6]$ with $NaVO_3$ (Kortz et al., Angew. Chem. Int. Ed. 2008, 47, pp. 793-796). The obtained polyanion has a decavanadate structure in which one of the two central addenda sites is occupied by platinum(IV).

However, there is still a need for late transition metal-containing POMs showing useful properties in homogeneous or heterogeneous catalytic applications.

Therefore, it is an object of the present invention to provide Group 9 to 11 transition metal-containing POMs which are useful as catalysts in homogeneous and heterogeneous oxidation reactions of organic substrates. Furthermore, such Group 9 to 11 transition metal-containing POMs should be easy and reproducible to prepare. Moreover, they should be useful as precursors for preparing mixed metal oxide catalysts and finely distributed metal clusters in a highly reproducible manner.

SUMMARY OF THE INVENTION

These objects, among others, are achieved by polyoxometalates represented by the formula $$(A_n)^{m+}[M_{13}X_8R_qO_y]^{m-}$$

or solvates thereof, wherein

A represents a cation, n is the number of the cations, m is the charge of the polyanion, M represents a transition metal selected from Pd, Pt, Au, Rh, Ir and mixtures thereof, X represents a heteroatom selected from As, Sb, Bi, P, Si, Ge, B, Al, Ga, S, Se, Te and mixtures thereof, R is a group covalently bound to X, provided X is P, As, Si or Ge, and is independently selected from the group consisting of H, alkyl, alkenyl, alkynyl, aryl, heteroaryl, cycloalkyl, heterocyclyl, arylalkyl, arylalkenyl, cycloalkylalkyl, heterocyclylalkyl and heteroarylalkyl, wherein each of said alkyl, alkenyl, alkynyl, aryl, heteroaryl, cycloalkyl and heterocyclyl can be unsubstituted or substituted with one or more groups which can be the same or different, each group being independently selected from the group consisting of halogen, alkyl, alkenyl, alkynyl, aryl, heteroaryl, cycloalkyl, heterocyclyl, arylalkyl, arylalkenyl, cycloalkylalkyl, heterocyclylalkyl, heteroarylalkyl, —CF$_3$, —OCF$_3$, —CN, —OR$^2$, —NR$^2$R$^3$, —C(O$_2$)R$^2$, —C(O)R$^2$, —C(O)NR$^2$R$^3$, —SO$_3$H, —SR$^2$, —S(O$_2$)R$^2$, —S(O$_2$)NR$^2$R$^3$, —N(R$^2$)S(O$_2$)R$^3$, —N(R$^2$)C(O)R$^3$, —N(R$^2$)C(O)NR$^2$R$^3$, —NO$_2$ and X-containing moieties through which a polyoxometalate molecule can be linked to one ore more other polyoxometalate molecules, each of R$^2$ and R$^3$ being independently selected from the group consisting of H, alkyl, aryl and cycloalkyl, q is the number of R ranging from 0 to 8, and y is the number of oxygen atoms ranging from 32 to 40.

The phrase "R is a group covalently bound to X, provided X is P, As, Si or Ge" means that when X is not P, As, Si or Ge an R group is not bound to the X, e.g., q is zero.

DETAILED DESCRIPTION

According to one embodiment, the POMs of the present invention are represented by the formula $$(A_n)^{m+}[M_{13}X_8O_{40}]^{m-},$$

wherein

A represents a cation, n is the number of the cations, m is the charge of the polyanion, M represents a transition metal selected from Pd, Pt, Au, Rh, Ir and mixtures thereof, and X represents a heteroatom selected from As$^V$, Sb$^V$, Bi$^V$, P$^V$ and mixtures thereof.

The polyanion $[M_{13}X_8R_qO_y]^{m-}$ of the POMs according to the invention has been found to show structural analogies to the Keggin anion described above. It comprises twelve transition metal atoms M forming a distorted icosahedron (or distorted cuboctahedron) around the thirteenth central transition metal atom. In contrast to all other known POMs in which the addenda atom geometry is distorted octahedral (or more rarely, tetrahedral, square-pyramidal, or seven-coordinate) the thirteen transition metal atoms M have a square-planar coordination sphere. The large positive charge of the transition metal cations is compensated by oxo anions resulting in a $\{M_{13}O_{32}\}^{x-}$ assembly having approximately cuboctahedral symmetry with, for example, x being 38 if M has an oxidation state of +2 and x being 25 if M has an oxidation state of +3.

If q is 0, the eight triangular faces of the $\{M_{13}O_{32}\}^{x-}$ cuboctahedron are each capped by a positively charged $XO_p^{v+}$ group to form a distorted cube $[M_{13}X_8O_y]^{m-}$ such as $[M_{13}X_8O_{y-6}(OH)_6]^{(m-6)-}$ like $[M_{13}X_8O_{34}(OH)_6]^{(m-6)-}$. In the above $XO_p^{v+}$ group, p is 1 if X is As$^V$, Sb$^V$, Bi$^V$, P$^V$, Si$^{IV}$, Ge$^{IV}$, B$^{III}$, Al$^{III}$, Ga$^{III}$, S$^{VI}$, Se$^{VI}$ and Te$^{VI}$. p is 0, i.e., no oxygen atom is present, if X is a heteroatom having a lone pair of electrons, i.e., X is As$^{III}$, Sb$^{III}$, Bi$^{III}$, Se$^{IV}$, and/or Te$^{IV}$. v is the positive charge of the $XO_p^{v+}$ group and is dependent on the oxidation state of X as well as the number of oxygen atoms p. If p is 1, then v is +1 (B$^{III}$, Al$^{III}$, Ga$^{III}$), +2 (Si$^{IV}$, Ge$^{IV}$), +3 (As$^V$, Sb$^V$, Bi$^V$, P$^V$) or +4 (S$^{VI}$, Se$^{VI}$, Te$^{IV}$). If p is 0, then v is equal to the oxidation state of X, such as +3 (As$^{III}$, Sb$^{III}$, Bi$^{III}$) or +4 (Se$^{IV}$, Te$^{IV}$).

Each of the eight triangular faces of the $\{M_{13}O_{32}\}^{x-}$ cuboctahedron can also be capped by a positively charged XR$^{t+}$ group to form a distorted cube $[M_{13}O_{32}(XR)_8]^{m-}$, wherein X is P$^V$, As$^V$, Si$^{IV}$ and/or Ge$^{IV}$ and R is as defined above such as —H, —C$_6$H$_5$, —CH$_3$, —C$_2$H$_5$, —CH$_2$COOH or —CH$_2$NH$_2$. t is the positive charge of the XR$^{t+}$ group and is dependent on the oxidation state of X. If X is P$^V$ or As$^V$, t is +4. If X is Si$^{IV}$ or Ge$^{IV}$, t is +3. Group R covalently bound to the heteroatom allows for tuning of (i) the steric and electrostatic parameters on the surface of the POM, and (ii) the solubility properties of the POM ranging from hydrophilic to hydrophobic. Moreover, if group R is substituted by one ore more X containing moieties, e.g., —PO$_3$H$_2$, —AsO$_3$H$_2$, —SiO$_3$H$_3$ or —GeO$_3$H$_3$, a POM molecule can be linked via such X containing moieties to one or more other POM molecules thus forming chains or networks of POM molecules.

The size of the present POMs has been found to be about 1 nm$^3$ determined by single-crystal X-ray diffraction analysis.

Figure 1:
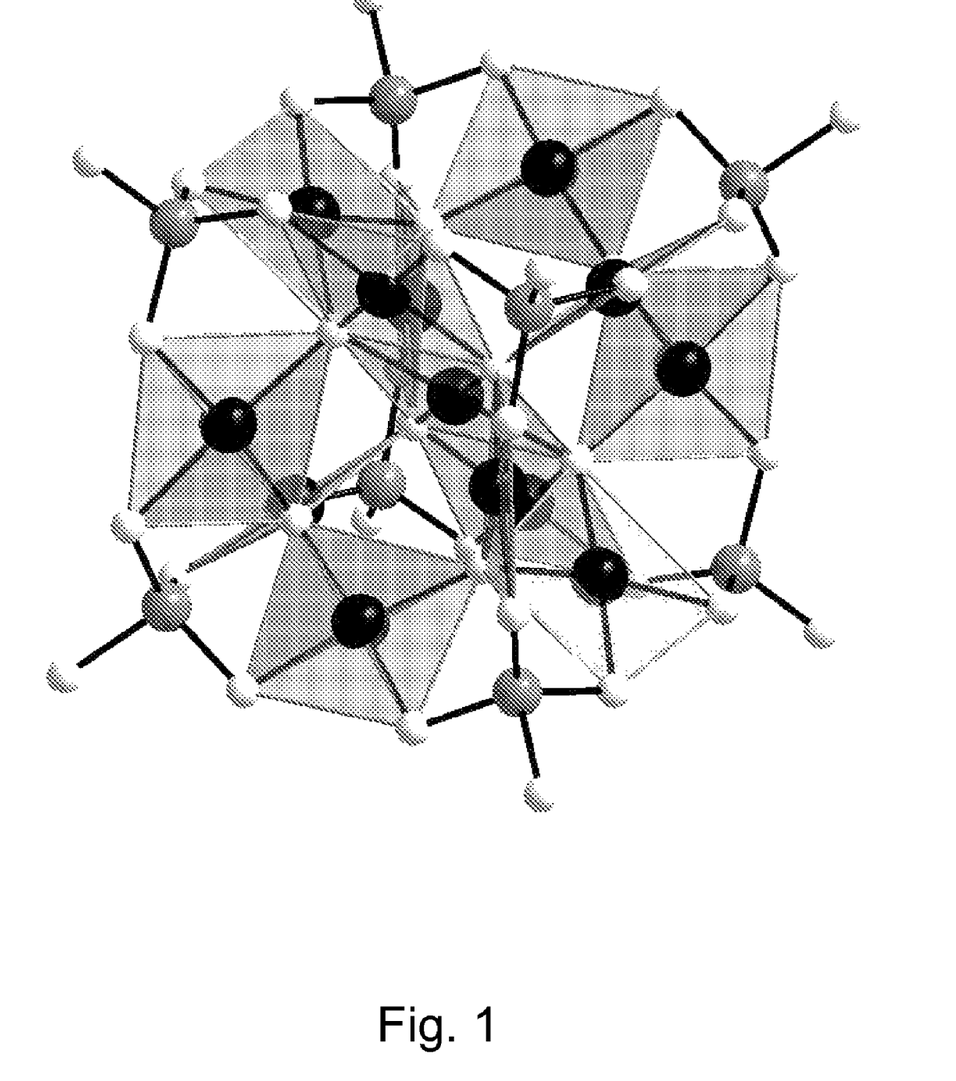
FIG. 1 is an illustration of the structure of the present polyanions.

The structure of the present polyanions is also illustrated in FIG. 1. The balls of this figure represent transition metal atoms M (black), heteroatoms X (grey shaded) and oxygen (white). The cations A, such as hydrogen atoms, are omitted for clarity.

In comparison to known TMPSs (transition metal-substituted polyoxometalates), the present POMs are characterized in that all addenda atoms of the POM framework are occupied by a transition metal selected from Groups 9 to 11 of the periodic table of the elements. Due to the exceptionally high concentration and accessibility of these transition metal cen- ters in the nanosized molecular entity described herein a unique catalytic performance in oxidation reactions is achieved.

The cation A can be hydrogen or a Group 1, 2, 3, 4, 5, 6, 7, 8, 9, 10, 11, 12, 13, 14, 15 and 16 metal or an organic cation. Preferably, A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium such as tetraalkylphosphonium, ammonium, guanidinium, tetraalkylammonium, protonated aliphatic amines, protonated aromatic amines or combinations thereof. More preferably, A is selected from hydrogen, sodium and combinations thereof.

The number n of cations is dependent on the nature of cation(s) A, namely its/their valence, and the negative charge m of the polyanion which has to be balanced. In any case, the overall charge of all cations A is equal to the charge of the polyanion. In turn, the charge m of the polyanion is dependent on the oxidation state of the transition metals M, the oxidation state of the heteroatoms X and the number of oxygen atoms y. Thus, m depends on the oxidation state of the atoms present in the polyanion, e.g., it follows from the oxidation states of O (−2), X (ranging from +3 to +6 such as +3 for B, Al, Ga, $As^{III}$, $Sb^{III}$ and $Bi^{III}$, +4 for Si, Ge, $Se^{IV}$ and $Te^{IV}$, +5 for $As^V$, $Sb^V$, $Bi^V$ and $P^V$ and +6 for S, $Se^{VI}$ and $Te^{VI}$), and M (ranging from +1 to +3 such as +1 for Rh and Ir, +2 for Pd and Pt, and +3 for Au). In some embodiments, m ranges from 1 to 43. In particular, m is 6, 9, 14, 22, 30 or 35. In a preferred embodiment, m is 14. Thus, n can generally range from 1 to 43. In particular, n ranges from 6 to 30 and more particularly is 6, 14, 22 or 30. In a preferred embodiment, n is 14.

Generally, A is acting as counterion of the polyanion and is therefore positioned outside of the POM framework. However, it is also possible that some of the cations A are located within the POM framework. In particular, if hydrogen is present as cation A, said hydrogen cation(s) can be covalently bound to oxygen atoms of the polyanion framework.

In such an embodiment, the POMs according to the invention can also be represented by the following formula such as e.g.

wherein
w is the number of hydrogen atoms bound to oxygen atoms of the polyanion framework, and A, n, m, M, X, R, q and y are defined as above.

Generally, w can range from 1 to m. Preferably, w ranges from 4 to 8 and more preferably is 6.

The transition metal M is selected from the group consisting of Pd, Pt, Rh, Ir, Au and mixtures thereof. In particular, the oxidation state of these metals is such that they have a square planar coordination sphere. Consequently, M is preferably selected from the group consisting of $Pd^{II}$, $Pt^{II}$, $Rh^I$, $Ir^I$, $Au^{III}$ and mixtures thereof. More preferably, M is $Pd^{II}$, $Pt^{II}$ or $Au^{III}$ and most preferably M is $Pd^{II}$.

Furthermore, the heteroatom X is selected from As, Sb, Bi, P, Si, Ge, B, Al, Ga, S, Se, Te and mixtures thereof. In particular, X is selected from the group consisting of $As^V$, $Sb^V$, $Bi^V$, $P^V$, $Si^{IV}$, $Ge^{IV}$, $B^{III}$, $Al^{III}$, $Ga^{III}$, $S^{VI}$, $Se^{VI}$, $Te^{VI}$, $As^{III}$, $Sb^{III}$, $Bi^{III}$, $Se^{IV}$, $Te^{IV}$ and mixtures thereof. Preferably, X is As and more preferably $As^V$. If a group R is covalently bound to X, X is selected from the group consisting of $P^V$, $As^V$, $Si^{IV}$ or $Ge^{IV}$.

R is hydrogen or an unsubstituted or substituted organic group as defined above. As used herein, "alkyl" represents a straight or branched aliphatic hydrocarbon group with 1 to about 20 carbon atoms. Preferred alkyl groups contain 1 to about 12 carbon atoms. More preferred alkyl groups contain 1 to about 6 carbon atoms. Non-limiting examples of suitable alkyl groups include methyl, ethyl, n-propyl, isopropyl and t-butyl. "Alkenyl" represents a straight or branched aliphatic hydrocarbon group containing at least one carbon-carbon double bond and having 2 to about 15 carbon atoms. Preferred alkenyl groups have 2 to about 12 carbon atoms; and more preferably 2 to about 4 carbon atoms. Non-limiting examples of suitable alkenyl groups include ethenyl, propenyl and 2-butenyl. "Alkynyl" represents a straight or branched aliphatic hydrocarbon group containing at least one carbon-carbon triple bond and having 2 to about 15 carbon atoms. Preferred alkynyl groups have 2 to about 12 carbon atoms; and more preferably 2 to about 4 carbon atoms in the chain. Non-limiting examples of suitable alkynyl groups include ethynyl, propynyl, 2-butynyl and 3-methylbutynyl. "Aryl" represents an aromatic monocyclic or multicyclic ring system comprising about 6 to about 14 carbon atoms, preferably about 6 to about 10 carbon atoms. Non-limiting examples of suitable aryl groups include phenyl and naphthyl. "Heteroaryl" represents an aromatic monocyclic or multicyclic ring system comprising about 5 to about 14 ring atoms, preferably about 5 to about 10 ring atoms, in which one or more of the ring atoms is an element other than carbon, for example, nitrogen, oxygen or sulfur, alone or in combination. Preferred heteroaryls contain about 5 to about 6 ring atoms. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. "Cycloalkyl" represents a non-aromatic mono- or multicyclic ring system comprising 3 to about 10 carbon atoms, preferably about 5 to about 10 carbon atoms. Preferred cycloalkyl rings contain about 5 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like. "Heterocyclyl" represents a non-aromatic saturated monocyclic or multicyclic ring system comprising 3 to about 10 ring atoms, preferably about 5 to about 10 ring atoms, in which one or more of the atoms in the ring system is an element other than carbon, for example, nitrogen, oxygen or sulfur, alone or in combination. Preferred heterocyclyls contain about 5 to about 6 ring atoms. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Arylalkyl" represents an aryl-alkyl-group in which the aryl and alkyl are as previously described. Non-limiting examples of suitable arylalkyl groups include benzyl, 2-phenethyl and naphthalenylmethyl. The bond to X is through the alkyl. Likewise, also "cycloalkylalkyl", "heterocyclylalkyl" and "heteroarylalkyl" are bound to X via the alkyl. In preferred embodiments, R is H, —CH$_3$, —C$_2$H$_5$, —C$_3$H$_7$, —C$_4$H$_9$, —C$_6$H$_5$, —CH$_2$COOH, —CH$_2$NH$_2$, —CH$_2$CH$_2$COOH, —CH$_2$CH$_2$Cl, —CH$_2$CH$_2$CH(NH$_2$)COOH, -(p-C$_6$H$_4$NH$_2$), -(p-C$_6$H$_4$NO$_2$), -(p-C$_6$H$_4$OH) or 3-nitro-4-hydroxyphenyl.

Generally, q is ranging from 0 to 8. In particular, q is 0 or 8. In a preferred embodiment q is 0, i.e. no group R is present. In another embodiment q is 1, 2, 3, 4 5, 6, 7, or 8.

The number of oxygen atoms y depends on the nature of the heteroatoms X and the number q of groups R present in the POM. If q is 0 and X is As$^V$, Sb$^V$, Bi$^V$, P$^V$, Si$^{IV}$, Ge$^{IV}$, B$^{III}$, Al$^{III}$, Ga$^{III}$, S$^{VI}$, Se$^{VI}$ or Te$^{VI}$, then y is 40. If q is 0 and X is As$^{III}$, Sb$^{III}$, Bi$^{III}$, Se$^{IV}$ or Te$^{IV}$, then y is 32. If q is 8, then X is P$^V$, As$^V$, Si$^{IV}$ or Ge$^{IV}$ and y is 32.

Accordingly, in a preferred embodiment the invention relates to POMs represented by the formula (A$_n$)$^{14+}$[Pd$_{13}$As$_8$O$_{40}$]$^{14-}$ or solvates thereof, wherein A and n are the same as defined above.

Further, suitable examples of POMs according to the invention are represented by the formula (A$_n$)$^{m+}$[Pd$_{13}$X$_8$R$_q$O$_y$]$^{m-}$, e.g.

(A$_n$)$^{m+}$[Pd$_{13}$X$_8$O$_y$]$^{m-}$, (A$_n$)$^{m+}$[Pd$_{13}$X$_8$O$_{40}$]$^{m-}$, (A$_n$)$^{14+}$[Pd$_{13}$X$_8$O$_{40}$]$^{14-}$, (A$_n$)$^{8+}$[Pd$_{13}$As$_8$O$_{34}$(OH)$_6$]$^{8-}$,

H$_6$Na$_8$[Pd$_{13}$As$_8$O$_{40}$] or

Na$_8$[Pd$_{13}$As$_8$O$_{34}$(OH)$_6$];

(A$_n$)$^{m+}$[Pt$_{13}$X$_8$R$_q$O$_y$]$^{m-}$, e.g.

(A$_n$)$^{m+}$[Pt$_{13}$X$_8$O$_y$]$^{m-}$, (A$_n$)$^{m+}$[Pt$_{13}$X$_8$O$_{40}$]$^{m-}$, (A$_n$)$^{14+}$[Pt$_{13}$X$_8$O$_{40}$]$^{14-}$, (A$_n$)$^{14+}$[Pt$_{13}$As$_8$O$_{40}$]$^{14-}$ such as (A$_n$)$^{8+}$[Pt$_{13}$As$_8$O$_{34}$(OH)$_6$]$^{8-}$, H$_6$Na$_8$[Pt$_{13}$As$_8$O$_{40}$] or Na$_8$[Pt$_{13}$As$_8$O$_{34}$(OH)$_6$]; and (A$_n$)$^{m+}$[Au$_{13}$X$_8$R$_q$O$_y$]$^{m-}$ such as (A$_n$)$^{m+}$[Au$_{13}$X$_8$O$_y$]$^{m-}$ or (A$_n$)$^{m+}$[Au$_{13}$X$_8$O$_{40}$]$^{m-}$.

The invention also includes solvates of the present POMs. A solvate is an association of solvent molecules with a POM. Preferably, water is associated with the POMs and thus, the POMs according to the invention can in particular be represented by the formula (A$_n$)$^{m+}$[M$_{13}$X$_8$R$_q$O$_y$]$^{m-}$.zH$_2$O, such as (A$_n$)$^{m+}$[M$_{13}$X$_8$O$_y$]$^{m-}$.zH$_2$O, (A$_n$)$^{m+}$[M$_{13}$X$_8$O$_{40}$]$^{m-}$.zH$_2$O or (A$_n$)$^{(m-w)+}$[M$_{13}$X$_8$O$_{(40-w)}$(OH)$_w$]$^{(m-w)-}$.zH$_2$O, wherein z represents the number of attracted water molecules per POM molecule and mostly depends on the type of cations A. In some embodiments z is an integer from 1 to 100 such as 42.

Suitable examples of the POM solvates according to the invention are represented by the formula (A$_n$)$^{m+}$[Pd$_{13}$X$_8$R$_q$O$_y$]$^{m-}$.zH$_2$O, e.g.

(A$_n$)$^{m+}$[Pd$_{13}$X$_8$O$_y$]$^{m-}$.zH$_2$O, (A$_n$)$^{m+}$[Pd$_{13}$X$_8$O$_{40}$]$^{m-}$.zH$_2$O, (A$_n$)$^{14+}$[Pd$_{13}$X$_8$O$_{40}$]$^{14-}$.zH$_2$O, (A$_n$)$^{14+}$[Pd$_{13}$As$_8$O$_{40}$]$^{14-}$.zH$_2$O such as (A$_n$)$^{8+}$[Pd$_{13}$As$_8$O$_{34}$(OH)$_6$]$^{8-}$.zH$_2$O, H$_6$Na$_8$[Pd$_{13}$As$_8$O$_{40}$].zH$_2$O, H$_6$Na$_8$[Pd$_{13}$As$_8$O$_{40}$].42 H$_2$O, Na$_8$[Pd$_{13}$As$_8$O$_{34}$(OH)$_6$].zH$_2$O and Na$_8$[Pd$_{13}$As$_8$O$_{34}$(OH)$_6$].42 H$_2$O.

The invention is further directed to a process for preparing polyoxometalates according to the invention comprising
(a) reacting a source of M with an X containing starting material to form a salt of [M$_{13}$X$_8$R$_q$O$_y$]$^{m-}$,
(b) filtering the reaction mixture of step (a),
(c) optionally adding a salt of A to the reaction mixture of step (a) or the filtrate obtained in step (b) to form (A$_n$)$^{m+}$[M$_{13}$X$_8$R$_q$O$_y$]$^{m-}$ or a solvate thereof, and
(d) optionally recovering the polyoxometalate obtained in step (b) or step (c),
wherein A, n, m, M, X, R, q and y are the same as defined above.

In step (a) of the present process a source of M is used. Generally, Pd$^{2-}$ salts such as PdCl$_2$, PdBr$_2$, PdI$_2$, Pd(CH$_3$COO)$_2$, PdSO$_4$, Pt$^{2+}$ salts such as PtCl$_2$, PtBr$_2$, PtI$_2$, Rh salts such as [(C$_6$H$_5$)$_3$P]$_2$RhCl(CO) and [Rh(CO)$_2$Cl]$_2$, Ir salts such as [(C$_6$H$_5$)$_3$P]$_2$IrCl(CO) and/or Au$^{3+}$ salts such as AuCl$_3$, AuBr$_3$, Au(OH)$_3$, HAuCl$_4$.aq, HAuBr$_4$.xH$_2$O can be used as a transition metal source. Preferably, the Pd source is PdCl$_2$ and the Pt source is PtCl$_2$.

The transition metal source is reacted with an X containing starting material. In particular, an oxide of X or an oxo acid of X is used as X containing starting material. It is also possible to use a water-soluble salt such as a halide of X. Suitable examples of X containing starting materials include X$_2$O$_5$ such as As$_2$O$_5$, P$_2$O$_5$, Sb$_2$O$_5$ or Bi$_2$O$_5$, X$_2$O$_3$ such as As$_2$O$_3$, Sb$_2$O$_3$ or Bi$_2$O$_3$, H$_3$BO$_3$, H$_3$PO$_4$, H$_3$PO$_3$, H$_2$SeO$_3$, H$_2$SeO$_4$, H$_2$TeO$_3$, H$_2$TeO$_4$, H$_2$SO$_4$, H$_4$SiO$_4$, Na$_4$SiO$_4$, AlCl$_3$, GaCl$_3$ and GeCl$_4$. It is preferred reacting the transition metal source, preferably PdCl$_2$, with As$_2$O$_5$.

If the resulting POM is to contain one or more groups R, the X containing starting material also contains R. In particular, an X containing starting material in which R is covalently bound to X is used. For example, R containing derivatives of phosphonic acid, arsonic acid, trichlorosilane and trichlorogermanium can be used. Examples of suitable XR containing starting materials include methylphosphonic acid, phosphonoacetic acid, 2-carboxyethylphosphonic acid, phenylphosphonic acid, methylarsonic acid, ethylarsonic acid, propylarsonic acid, butylarsonic acid, p-arsanilic acid, DL-2-amino-4-arsonobutanoic acid monohydrate, p-aminophenylarsonic acid, ammonium 4-nitrophenylarsonate, ammonium-4-hydroxyphenyl-arsonic acid chloride dihydrate, 3-nitro-4-hydroxyphenylarsonic acid, 4-hydroxyphenylarsonic acid, methyltrichlorosilane, ethyltrichlorosilane, b-chloroethyltrichlorosilane, phenyltrichlorosilane, methylgermanium trichloride, ethylgermanium trichloride, phenylgermanium trichloride and methylgermanium triiodide. In order to link a POM molecule with at least one other POM molecule R can be substituted with at least one further X containing moiety. Examples of X—R—X containing starting materials which can be used in step (a) include methylenediphosphonic acid, 1,2-ethylenediphosphonic acid, 2-hydroxypropane-1,3-bis (arsonic acid), 1R(S),2S(R)-1,2-bis(trichlorosilyl)-1,2-diphenylethane, 1,3-bis(trichlorosilylmethyl)benzene, 1,4-bis(trichlorosilylmethyl)benzene and 1,1,1,4,4,4-hexachloro-1,4-disilabutane. Suitable examples of X containing starting materials which comprise more than two X moieties include nitrilotris(methylphosphonic acid) and hexakis(3-(trichlorosilyl)propyl)benzene. Preferably, the X containing starting material which also contains R is water soluble.

In a preferred embodiment, step (a) is carried out in an aqueous solution. If the X containing starting material has only a low solubility in water (for example, because it also contains one or more groups R) it is possible to dissolve the X containing starting material in a small volume of organic solvent and then adding this solution to an aqueous solution of the source of M. Examples of suitable organic solvents include, but are not limited to acetonitrile, acetone, toluene, DMF, DMSO, ethanol, methanol, n-butanol, sec-butanol, isobutanol and mixtures thereof. It is also possible to use emulsifying agents to allow the reagents of step (a) to undergo a reaction.

The pH of the aqueous solution usually used in step (a) ranges from 2 to 14, preferably from 4 to 8 and more preferably from 5 to 7. Most preferably, a pH of about 6.1 is used. Generally, a buffer solution can be used for adjusting the pH. It is particularly preferred to use a sodium acetate buffer having a concentration of 0.5 M and a pH of about 6.1 as aqueous solvent. In another embodiment, the concentration of the aqueous buffer solution (preferably a sodium acetate buffer solution) is from 0.1 to 2 M, preferably 0.25 to 1.5 M, preferably from 0.5 to 1.0 M, preferably about 0.5 M.

Moreover, in step (a) it is preferred that the concentration of the M ions originating from the transition metal source ranges from 0.01 to 1 mol/L, preferably 0.05 to 0.5 mol/L, more preferably 0.1 to 0.15 mol/L, whereas the concentration of the X containing starting material preferably ranges from 0.007 to 7 mol/L, more preferably 0.03 to 0.3 mol/L or 0.05 to 0.1 mol/L. The molar ratio between the M ions originating from the transition metal source and X originating from the X containing starting material preferably ranges from 6:2 to 1:2, more preferably 4:2 to 1:1 and most preferably is about 3:2.

Furthermore, it is preferred that the reaction mixture is heated during step (a). Preferably, the reaction of the source of M and the X containing starting material is performed at a temperature of 20 to 100° C., preferably 70 to 90° C. Moreover, the reaction mixture is preferably heated for about 10 min to about 4 h, more preferably for about 30 min to 2 h, most preferably for about 1.5 h. Further, it is preferred that the reaction mixture is stirred during step (a).

In step (b), the reaction mixture is filtered. Preferably, the reaction mixture is filtered immediately after the end of step (a), i.e. immediately after the stirring is turned off, and is then optionally cooled. Alternatively, the heated reaction mixture is cooled first, preferably to room temperature, and subsequently filtered.

Furthermore, in step (c) a salt of the cation A can be added to the reaction mixture of step (a) or to its filtrate obtained in step (b) to form $(A_n)^{m+}[M_{13}X_8R_qO_{40}]^{m-}$. Preferably, the salt of A is added as a solid or in the form of an aqueous solution. The counterions of A can be selected from the group consisting of any stable, non-reducing, water soluble anion, e.g., halides, nitrate, sulfate, acetate. Preferably, the chloride salt is used. However, the addition of extra cations A in step (c) is not necessary if the desired cations are already present during step (a), for example, as a component of the buffer used as solvent in step (a) or a component of the transition metal source including, for example, palladium and platinum themselves. Preferably, all desired cations are already present during step (a) so that there is no optional addition of extra cations.

In step (d), the POMs according to the invention formed in step (b) or (c) can be recovered. For example, isolation of the POMs can be effected by common techniques including bulk precipitation or crystallization.

The invention is also directed to the use of POMs according to the invention for catalyzing homogeneous and heterogeneous oxidation reactions of organic substrates. In particular, the present POMs can be used for oxidizing unsubstituted and substituted hydrocarbons such as branched or unbranched alkanes and alkenes having carbon numbers from C1 to C20, preferably from C1 to C6, cycloalkanes, cycloalkenes, aromatic hydrocarbons or mixtures thereof. Examples of suitable organic substrates are methane, ethane, propane, butane, isobutane, pentane, isopentane, neopentane, hexane, ethylene, propylene, α-butylene, cis-β-butylene, trans-β-butylene, isobutylene, n-pentylene, isopentylene, cyclohexane, adamantane, cyclooctadiene, benzene, toluene, o-xylene, m-xylene, p-xylene, mesitylene, durene, hexamethylbenzene, naphthalene, anthracene, phenantrene and mixtures thereof. Since the external, square-planar palladium or platinum ions are not sterically shielded by the polyanion backbone, the coordination sites of palladium and platinum, respectively, are easily accessible to the organic substrate and the oxygen transfer molecule and therefore high catalytic activities are achieved. Further, the remarkable thermal stability of the POMs permits their use under a great variety of reaction conditions.

Figure 2:
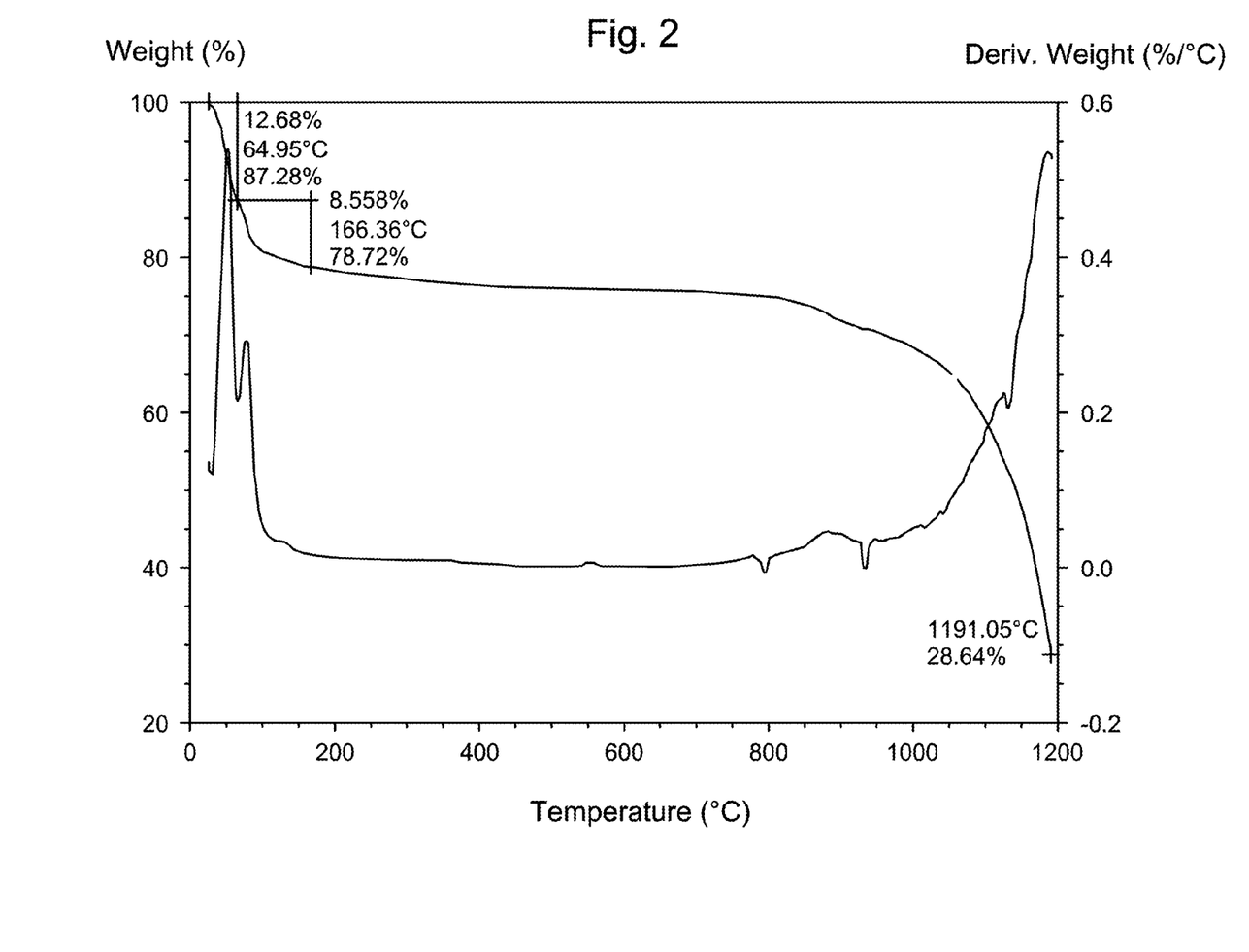
FIG. 2 is a plot of a thermogravimetric analysis of a POM according to the invention.

Prior to their use in oxidation reactions, the present POMs can be supported on a solid support. Suitable supports include materials having a high surface area and a pore size which is sufficient to allow the POMs to be loaded, e.g., aerogels of aluminum oxide and magnesium oxide, titanium oxide, zirconium oxide, silica, mesoporous silica, active carbon, zeolites and mesoporous materials. In another embodiment, the supported POMs are further calcined at a temperature not exceeding the transformation temperature of the POM, i.e., the temperature at which decomposition of the POM starts to take place (usually about 700° C. for the present POMs according to thermogravimetric analysis (TGA), as illustrated in FIG. 2).

If supported, POM loading levels on the support are typically up to 40 wt. % or even more. Accordingly, POM loading levels on the support of 1 to 40 wt. %, particularly 5 to 30 wt. %, and more particularly 5 to 20 wt. % are in general suitable. POM loading levels can be determined by Inductively Coupled Plasma Mass Spectrometry (ICP-MS) analysis or X-ray photoelectron spectroscopy (XPS). In the event the values from the ICP and XPS differ, the ICP shall control. ICP analysis is performed using a Varian Vista MPX. The samples are prepared using microwave digestion by dissolving 10 mg of the supported POM in a mixture of $HNO_3$ (6 ml), HCl (6 ml), HF (1 ml) and $H_2O_2$ (3 ml). After the first run, 6 ml of boric acid (5%) is added and a second run is performed. The quantification is done by Inductively Coupled Plasma Optical Emission Spectrometry (ICP-OES) using calibration curves made between 0 and 50 ppm from standards with known amounts of the respective elements. All tests are conducted twice using a 20 mg sample in the second test. The final volume for each sample is 100 ml.

If the present POMs are used for catalyzing homogeneous and heterogeneous oxidation reactions of organic substrates, commonly suitable oxygen donors such as molecular oxygen, peroxides (e.g., $H_2O_2$, t-$(C_4H_9)$OOH) or peracids (e.g. $CH_3COOOH$) can be used as oxidizing agent. Preferably, the oxidizing agent is an oxygen containing atmosphere. In particular, the oxygen containing atmosphere is air and is preferably constantly passed through the organic substrate (such as an alkane or alkene) at a pressure of 0.01 to 100 bar (1 to 10,000 kPa), preferably 10 to 70 bar (1000 to 7000 kPa).

Moreover, in some embodiments, the oxidation of the organic substrate is preferably carried out at a temperature of 30 to 600° C., preferably 75 to 250° C., preferably 130 to 180° C. In a particularly useful embodiment the oxidation is carried out at a temperature of 100° C. or more, alternately 110° C. or more, alternately 120° C. or more, alternately 130° C. or more, alternately 140° C. or more, alternately 150° C. or more, alternately 160° C. or more, alternately 170° C. or more, alternately 180° C. or more, alternately 190° C. or more, alternately 200° C. or more, alternately 210° C. or more, alternately 220° C. or more.

For example, the POMs according to the invention can be collected after an oxidation reaction, washed with a polar or non-polar solvent such as acetone then dried under heat (typically 50° C. or more, alternately 100° C. or more, alternately 125° C. or more, alternately 150° C. or more) for 30 minutes to 48 hours, typically for 1 to 24 hours, more typically for 2 to 10 hours, more typically for 3 to 5 hours. The recycled supported POMs may be used on fresh organic molecules (such as hexadecane) or on recycled organic molecules from a recycle stream.

Advantageously, the supported POMs may be recycled and used again under the same or different reaction conditions. Typically the supported POMs are recycled at least 1 time, preferably at least 4 times, preferably at least 8 times, preferably at least 12 times, preferably at least 100 times.

Thus, this invention also relates to a process for oxidizing organic substrates (typically an alkane) which process comprises contacting a first organic substrate with one or more POMs described herein, thereafter recovering the POMs, contacting the POMs with a solvent (such as acetone) at a temperature of 50° C. or more to obtain a recycled POM, thereafter contacting the recycled POM with a second organic substrate, which may be the same as or different from the first organic substrate, this process may be repeated many times, preferably at least 4 times, preferably at least 8 times, preferably at least 12 times, preferably at least 100 times.

Due to the definite stoichiometry of POMs, the present POMs can be converted (e.g., by calcination at a temperature exceeding the transformation temperature) to mixed metal oxide catalysts in a highly reproducible manner. Consequently, the POMs according to the invention can also be used as a precursor for mixed metal oxide catalysts such as so-called Mitsubishi-type catalysts which are particularly useful for the oxidation of hydrocarbons such as propane.

Furthermore, due to the fact that all addenda atoms of the POM framework are occupied by a transition metal M, the present POMs can also be used as a precursor for the design of unsupported or supported nanocatalysts of M at the atomic or molecular level, i.e., particles of M having an average diameter of 0.5 to 10 nm, obtained by reduction of the POM.

In particular, the present POMs can be supported on a matrix surface in a highly dispersed form. Examples of suitable matrix surfaces include, but are not limited to polymers, graphite, carbon nanotubes, electrode surfaces, aerogels of aluminum oxide and magnesium oxide, titanium oxide, zirconium oxide, silica, mesoporous silica, active carbon, zeolites and mesoporous materials. In a next step, the supported POMs can be reduced to give monodisperse particles of $M^0$ such as $Pd^0$. According to one embodiment, the reduction of the supported POMs can be effected by electrochemical reduction. It is also possible to chemically reduce the supported POMs. Such a chemical reduction can for example be effected by using borohydrides, aluminohydrides, hydrazine, CO or flowing hydrogen at elevated temperature and pressure. The obtained nanoparticles of $M^0$ can be used for a wide range of catalytic applications such as in fuel cells, for detection of organic substrates, selective hydrogenation, reforming and oligomerization. Besides supporting the present POMs on a matrix surface and subsequently reducing them, the deposition of the POMs on a surface matrix and their reduction can also be carried out simultaneously. Alternatively, the present POMs can firstly be reduced and subsequently a suspension of the reduced POM metal clusters can be applied to a suitable support. Thus, the present POMs can be used a precursor for preparing a nanocatalyst of M which is obtained by (i) supporting the POM on a solid support and subsequently reducing the supported POM, (ii) reducing the POM and subsequently supporting the reduced POM on a solid support or (iii) simultaneously reducing the POM and supporting it on a solid support.

For example, the POMs according to the invention such as $[Pd_{13}As_8O_{34}(OH)_6]^{8-}$ can be used to produce modified electrodes by electrochemical deposition of the POM on an electrode surface such as a glassy carbon (GC) electrode surface. The obtained deposits contain essentially $M^0$ such as $Pd^0$ with very small amounts of $M^{x+}$ such as $Pd^{2+}$ and exhibit improved electrochemical behaviors like improved kinetics of electrocatalytic processes compared to a film deposited using a conventional precursor of M. For example, electrodes modified with a deposit of the present POMs can be used for the electrochemical oxidation of hydrazine. It has been found that such modified electrodes show a very small overpotential and a remarkably high shelf life. Further, it has been found that there is a good linearity between the oxidation peak current intensity and the concentration of hydrazine.

In another embodiment, this invention relates to:
1. Polyoxometalate (POM) represented by the formula $$(A_n)^{m+}[M_{13}X_8R_qO_y]^{m-}$$

or solvates thereof, wherein
A represents a cation,
n is the number of the cations,
m is the charge of the polyanion,
M represents a transition metal selected from Pd, Pt, Au, Rh, Ir and mixtures thereof,
X represents a heteroatom selected from As, Sb, Bi, P, Si, Ge, B, Al, Ga, S, Se, Te and mixtures thereof,
R is a group covalently bound to X, provided X is P, As, Si or Ge, and is independently selected from the group consisting of H, alkyl, alkenyl, alkynyl, aryl, heteroaryl, cycloalkyl, heterocyclyl, arylalkyl, arylalkenyl, cycloalkylalkyl, heterocyclylalkyl and heteroarylalkyl, wherein each of said alkyl, alkenyl, alkynyl, aryl, heteroaryl, cycloalkyl and heterocyclyl can be unsubstituted or substituted with one or more groups which can be the same or different, each group being independently selected from the group consisting of halogen, alkyl, alkenyl, alkynyl, aryl, heteroaryl, cycloalkyl, heterocyclyl, arylalkyl, arylalkenyl, cycloalkylalkyl, heterocyclylalkyl, heteroarylalkyl, —CF$_3$, —OCF$_3$, —CN, —OR$^2$, —NR$^2$R$^3$, —C(O$_2$)R$^2$, —C(O)R$^2$, —C(O)NR$^2$R$^3$, —SO$_3$H, —SR$^2$, —S(O$_2$)R$^2$, —S(O$_2$)NR$^2$R$^3$, —N(R$^2$)S(O$_2$)R$^3$, —N(R$^2$)C(O)R$^3$, —N(R$^2$)C(O)NR$^2$R$^3$, —NO$_2$ and X-containing moieties through which a polyoxometalate molecule can be linked to one ore more other polyoxometalate molecules, each of R$^2$ and R$^3$ being independently selected from the group consisting of H, alkyl, aryl and cycloalkyl, q is the number of R ranging from 0 to 8, and y is the number of oxygen atoms ranging from 32 to 40.

2. Polyoxometalate according to paragraph 1, wherein M is Pd.

3. Polyoxometalate according to paragraph 1 or 2, wherein X is As.

4. Polyoxometalate according to any one of paragraphs 1 to 3, wherein y is 40 and q is 0.

5. Polyoxometalate according to any one of paragraphs 1 to 4, wherein A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines or combinations thereof.

6. Polyoxymetalate according to any one of paragraphs 1 to 5, represented by the formula $$(A_n)^{(m-w)+}[M_{13}X_8R_qO_{(y-w)}(OH)_w]^{(m-w)-},$$

wherein w is the number of hydrogen atoms bound to oxygen atoms of the polyanion framework and ranges from 1 to m.

7. Polyoxometalate according to any one of paragraphs 1 to 6, represented by the formula $$(A_n)^{m+}[M_{13}X_8R_qO_y]^{m-} \cdot zH_2O,$$

wherein z represents the number of attracted water molecules per polyoxometalate molecule and ranges from 1 to 100.

8. Process for the preparation of a polyoxometalate according to any one of paragraphs 1 to 7 comprising (a) reacting a source of M with an X containing starting material to form a salt of $[M_{13}X_8R_qO_y]^{m-}$, (b) filtering the reaction mixture of step (a), (c) optionally adding a salt of A to the reaction mixture of step (a) or the filtrate obtained in step (b) to form $(A_n)^{m+}[M_{13}X_8R_qO_y]^{m-}$ or a solvate thereof, and (d) optionally recovering the polyoxometalate obtained in step (b) or step (c), wherein A, n, m, M, X, R, q and y are the same as defined in claims 1 to 7.

9. Process according to paragraph 8, wherein the source of M is selected from the group consisting of PdCl$_2$, PdBr$_2$, PdI$_2$, Pd(CH$_3$COO)$_2$, PdSO$_4$, PtCl$_2$, PtBr$_2$, PtI$_2$, [(C$_6$H$_5$)$_3$P]$_2$RhCl(CO), [Rh(CO)$_2$Cl]$_2$, [(C$_6$H$_5$)$_3$P]$_2$IrCl(CO), AuCl$_3$, AuBr$_3$, Au(OH)$_3$, HAuCl$_4$.aq, HAuBr$_4$.xH$_2$O and mixtures thereof, and preferably is PdCl$_2$.

10. Process according to paragraph 8 or 9, wherein the X containing starting material is an oxide of X and preferably is As$_2$O$_5$.

11. Process according to any one of paragraphs 8 to 10, wherein step (a) is carried out in an aqueous solution and the pH of the aqueous solution ranges from 2 to 14, preferably from 4 to 8.

12. Process according to paragraph 11, wherein in step (a) a sodium acetate buffer having a concentration of 0.5 M and a pH of about 6.1 is used as aqueous solution.

13. Process according to any one of paragraphs 8 to 12, wherein in step (a) the concentration of the transition metal ions originating from the source of M ranges from 0.01 to 1 mol/L and the concentration of the X containing starting material ranges from 0.007 to 7 mol/L.

14. Process according to any one of paragraphs 8 to 13, wherein in step (a) the reaction mixture is heated to a temperature of 20 to 100° C., preferably from 70 to 90° C.

15. Process according to any one of paragraphs 8 to 14, wherein in step (d) the product is isolated by bulk precipitation or crystallization.

16. Use of a polyoxometalate according to any one of paragraphs 1 to 7 or prepared according to any one of claims 8 to 15 as catalyst for the homogeneous or heterogeneous oxidation of organic substrates.

17. Use according to paragraph 16, wherein the organic substrates are unsubstituted or substituted hydrocarbons such as branched or unbranched alkanes and alkenes having carbon numbers from C1 to C20, cycloalkanes, cycloalkenes, aromatic hydrocarbons or mixtures thereof.

18. Use according to paragraph 16 or 17, wherein the polyoxometalate is supported on a solid support.

19. Use according to paragraph 18, wherein the supported polyoxometalate is calcined at a temperature not exceeding the transformation temperature of the polyoxometalate.

20. Process for oxidizing organic substrates comprising:

(i) contacting a first organic substrate with one or more polyoxometalates according to any one of paragraphs 1 to 7 or prepared according to any one of paragraphs 8 to 15, (ii) recovering the polyoxometalates, (iii) contacting the polyoxometalates with a solvent at a temperature of 50° C. or more to obtain a recycled polyoxometalate, (iv) contacting the recycled polyoxometalate with a second organic substrate, which may be the same as or different from the first organic substrate, and (v) optionally repeating steps (ii) to (iv).

21. Use of a polyoxometalate according to any one of paragraphs 1 to 7 or prepared according to any one of paragraphs 8 to 15 as a precursor for preparing mixed metal oxide catalysts.

22. Use according to paragraph 21, wherein the mixed metal oxide catalysts are Mitsubishi-type catalysts.

23. Use of a polyoxometalate according to any one of paragraphs 1 to 7 or prepared according to any one of paragraphs 8 to 15 as a precursor for preparing a nanocatalyst of M, wherein M is the same as defined in paragraphs 1 to 7 and the nanocatalyst is obtained by reduction of the polyoxometalate.

The invention is further illustrated by the following example.

EXAMPLE 1

Synthesis of Na$_8$ [Pd$_{13}$As$_8$O$_{34}$(OH)$_6$].42 H$_2$O

A sample of 0.110 g (0.62 mmol) PdCl$_2$ and a sample of 0.044 g (0.191 mmol) As$_2$O$_5$ were dissolved in 5 mL of 0.5 M sodium acetate buffer solution (pH=6.1). While stirring, the solution was heated to 80° C. for 90 minutes. Gradually the colour of the solution became dark red-brown. Then, the solution was cooled to room temperature and filtered off. To crystallize the product, the filtrate was placed in crystallization vials and evaporated at room temperature in air. Within 4 to 24 hours, dark red-brown crystalline product was formed (yield: 0.05 g, 28%).

IR (cm-1): 860 (m), 800 (s), 667 (m), 654 (sh), 621 (m), 542 (s), 526 (sh), 474 (sh), 459 (sh), 420 (w) (measured on a Nicolet-Avatar 370 spectrometer using KBr pellets).

Anal. Calcd. for $Na_8[Pd_{13}As_8O_{34}(OH)_6].42\ H_2O$ (in %): Na, 5.15; Pd, 38.8; As, 16.80. Found: Na, 5.25; Pd, 38.7; As, 16.80. (M.W.=3568 g/mol).

The crystal water content of $Na_8[Pd_{13}As_8O_{34}(OH)_6].42\ H_2O$ was determined by TGA using a TA Instruments machine. A single dehydration step was observed which was complete at ~170° C. (FIG. 2).

Besides IR, elemental analysis and TGA the product was also characterized by single-crystal XRD. The crystal data and structure refinement obtained on a Bruker Kappa APEX II instrument using the SHELXTL software package are shown in the following Table.

TABLE 1

Crystal data and structure refinement for $Na_8[Pd_{13}As_8O_{34}(OH)_6]$ 42 $H_2O$.

| | |
|---|---|
| Empirical formula | H90 As8 Na8 O82 Pd13 |
| Formula weight | 3568 g/mol |
| Temperature | 296(2) K |
| Wavelength | 0.71073 Å |
| Crystal system | Triclinic |
| Space group | P-1 |
| Unit cell dimensions | a = 12.7477(8) Å α = 105.069(5)°. |
| | b = 13.1633(10) Å β = 109.731(5)°. |
| | c = 14.4539(16) Å γ = 105.814(4)°. |
| Volume | 2023.9(3) Å$^3$ |
| Z | 1 |
| Density (calculated) | 2.851 Mg/m$^3$ |
| Absorption coefficient | 6.222 mm$^{-1}$ |
| F(000) | 1642 |
| Crystal size | 0.11 × 0.06 × 0.05 mm$^3$ |
| Theta range for data collection | 3.73 to 27.49°. |
| Index ranges | -16 <= h <= 16, -17 <= k <= 17, -18 <= l <= 18 |
| Reflections collected | 90737 |
| Independent reflections | 9204 [R(int) = 0.1185] |
| Completeness to theta = 27.49° | 99.2% |
| Absorption correction | Semi-empirical from equivalents |
| Max. and min. transmission | 0.7260 and 0.4019 |
| Refinement method | Full-matrix least-squares on F$^2$ |
| Data/restraints/parameters | 9204/0/493 |
| Goodness-of-fit on F$^2$ | 1.029 |
| Final R indices [I > 2sigma(I)] | R1 = 0.0450, wR2 = 0.1055 |
| R indices (all data) | R1 = 0.0820, wR2 = 0.1221 |
| Largest diff. peak and hole | 1.964 and -1.222 e.Å$^{-3}$ |
| Data/restraints/parameters | 14333/0/492 |
| Goodness-of-fit on F$^2$ | 1.018 |
| Final R indices [I > 2sigma(I)] | R1 = 0.0593, wR2 = 0.1592 |
| R indices (all data) | R1 = 0.0886, wR2 = 0.1828 |
| Largest diff. peak and hole | 4.198 and -3.478 e.Å$^{-3}$ |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. Polyoxometalate (POM) represented by the formula $$(A_n)^{m+}[M_{13}X_8R_qO_y]^{m-}$$

or solvates thereof, wherein
A represents a cation,
n is the number of the cations,
m is the charge of the polyanion,
M represents a transition metal selected from Pd, Pt, Au, Rh, Ir and mixtures thereof,
X represents a heteroatom selected from As, Sb, Bi, P, Si, Ge, B, Al, Ga, S, Se, Te and mixtures thereof,
R is a group covalently bound to X, provided X is P, As, Si or Ge, and is independently selected from the group consisting of H, alkyl, alkenyl, alkynyl, aryl, heteroaryl, cycloalkyl, heterocyclyl, arylalkyl, arylalkenyl, cycloalkylalkyl, heterocyclylalkyl and heteroarylalkyl, wherein each of said alkyl, alkenyl, alkynyl, aryl, heteroaryl, cycloalkyl and heterocyclyl can be unsubstituted or substituted with one or more groups which can be the same or different, each group being independently selected from the group consisting of halogen, alkyl, alkenyl, alkynyl, aryl, heteroaryl, cycloalkyl, heterocyclyl, arylalkyl, arylalkenyl, cycloalkylalkyl, heterocyclylalkyl, heteroarylalkyl, —$CF_3$, —$OCF_3$, —CN, —$OR^2$, —$NR^2R^3$, —$C(O_2)R^2$, —$C(O)R^2$, —$C(O)NR^2R^3$, —$SO_3H$, —$SR^2$, —$S(O_2)R^2$, —$S(O_2)NR^2R^3$, —$N(R^2)S(O_2)R^3$, —$N(R^2)C(O)R^3$, —$N(R^2)C(O)NR^2R^3$, —$NO_2$ and X-containing moieties through which a polyoxometalate molecule can be linked to one ore more other polyoxometalate molecules, each of $R^2$ and $R^3$ being independently selected from the group consisting of H, alkyl, aryl and cycloalkyl,
q is the number of R ranging from 0 to 8 and
y is the number of oxygen atoms ranging from 32 to 40.

2. Polyoxometalate according to claim 1, wherein M is Pd.

3. Polyoxometalate according to claim 1, wherein X is As.

4. Polyoxometalate according to claim 1, wherein y is 40 and q is 0.

5. Polyoxometalate according to claim 1, wherein A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

6. Polyoxymetalate according to claim 1, represented by the formula $$(A_n)^{(m-w)+}[M_{13}X_8R_qO_{(y-w)}(OH)_w]^{(m-w)-},$$

wherein
w is the number of hydrogen atoms bound to oxygen atoms of the polyanion framework and ranges from 1 to m.

7. Polyoxometalate according to claim 1, represented by the formula $$(A_n)^{m+}[M_{13}X_8R_qO_y]^{m-}.zH_2O,$$

wherein z represents the number of attracted water molecules per polyoxometalate molecule and ranges from 1 to 100.

8. Process for the preparation of a polyoxometalate represented by the formula $$(A_n)^{m+}[M_{13}X_8R_qO_y]^{m-}$$

or solvates thereof, wherein

A represents a cation, n is the number of the cations, m is the charge of the polyanion, M represents a transition metal selected from Pd, Pt, Au, Rh, Ir and mixtures thereof, X represents a heteroatom selected from As, Sb, Bi, P, Si, Ge, B, Al, Ga, S, Se, Te and mixtures thereof, R is a group covalently bound to X, provided X is P, As, Si or Ge, and is independently selected from the group consisting of H, alkyl, alkenyl, alkynyl, aryl, heteroaryl, cycloalkyl, heterocyclyl, arylalkyl, arylalkenyl, cycloalkylalkyl, heterocyclylalkyl and heteroarylalkyl, wherein each of said alkyl, alkenyl, alkynyl, aryl, heteroaryl, cycloalkyl and heterocyclyl can be unsubstituted or substituted with one or more groups which can be the same or different, each group being independently selected from the group consisting of halogen, alkyl, alkenyl, alkynyl, aryl, heteroaryl, cycloalkyl, heterocyclyl, arylalkyl, arylalkenyl, cycloalkylalkyl, heterocyclylalkyl, heteroarylalkyl, —CF$_3$, —OCF$_3$, —CN, —OR$^2$, —NR$^2$R$^3$, —C(O$_2$)R$^2$, —C(O)R$^2$, —C(O)NR$^2$R$^3$, —SO$_3$H, —SR$^2$, —S(O$_2$)R$^2$, —S(O$_2$)NR$^2$R$^3$, —N(R$^2$)S(O$_2$)R$^3$, —N(R$^2$)C(O)R$^3$, —N(R$^2$)C(O)NR$^2$R$^3$, —NO$_2$ and X-containing moieties through which a polyoxometalate molecule can be linked to one ore more other polyoxometalate molecules, each of R$^2$ and R$^3$ being independently selected from the group consisting of H, alkyl, aryl and cycloalkyl, q is the number of R ranging from 0 to 8 and y is the number of oxygen atoms ranging from 32 to 40, said process comprising:

(a) reacting a source of M with an X containing starting material to form a salt of $[M_{13}X_8R_qO_y]^{m-}$, (b) filtering the reaction mixture of step (a), (c) optionally adding a salt of A to the reaction mixture of step (a) or the filtrate obtained in step (b) to form $(A_n)^{m+}[M_{13}X_8R_qO_y]^{m-}$ or a solvate thereof, and (d) optionally recovering the polyoxometalate obtained in step (b) or step (c).

9. Process according to claim 8, wherein the source of M is selected from the group consisting of PdCl$_2$, PdBr$_2$, PdI$_2$, Pd(CH$_3$COO)$_2$, PdSO$_4$, PtCl$_2$, PtBr$_2$, PtI$_2$, [(C$_6$H$_5$)$_3$P]$_2$RhCl(CO), [Rh(CO)$_2$Cl]$_2$, [(C$_6$H$_5$)$_3$P]$_2$IrCl(CO), AuCl$_3$, AuBr$_3$, Au(OH)$_3$, HAuCl$_4$.aq, HAuBr$_4$.xH$_2$O and mixtures thereof.

10. Process according to claim 8, wherein the X containing starting material is an oxide of X and preferably is As$_2$O$_5$.

11. Process according to claim 8, wherein step (a) is carried out in an aqueous solution and the pH of the aqueous solution ranges from 2 to 14, preferably from 4 to 8.

12. Process according to claim 11, wherein in step (a) a sodium acetate buffer having a concentration of 0.5 M and a pH of about 6.1 is used as aqueous solution.

13. Process according to claim 8, wherein in step (a) the concentration of the transition metal ions originating from the source of M ranges from 0.01 to 1 mol/L and the concentration of the X containing starting material ranges from 0.007 to 7 mol/L.

14. Process according to claim 8, wherein in step (a) the reaction mixture is heated to a temperature of 20 to 100° C., preferably from 70 to 90° C.

15. Process according to claim 8, wherein in step (d) the product is isolated by bulk precipitation or crystallization.

16. A process for the homogeneous or heterogeneous oxidation of organic substrates comprising contacting the substrate with polyoxometalate represented by the formula or solvates thereof, wherein A represents a cation, n is the number of the cations, m is the charge of the polyanion, M represents a transition metal selected from Pd, Pt, Au, Rh, Ir and mixtures thereof, X represents a heteroatom selected from As, Sb, Bi, P, Si, Ge, B, Al, Ga, S, Se, Te and mixtures thereof, R is a group covalently bound to X, provided X is P, As, Si or Ge, and is independently selected from the group consisting of H, alkyl, alkenyl, alkynyl, aryl, heteroaryl, cycloalkyl, heterocyclyl, arylalkyl, arylalkenyl, cycloalkylalkyl, heterocyclylalkyl and heteroarylalkyl, wherein each of said alkyl, alkenyl, alkynyl, aryl, heteroaryl, cycloalkyl and heterocyclyl can be unsubstituted or substituted with one or more groups which can be the same or different, each group being independently selected from the group consisting of halogen, alkyl, alkenyl, alkynyl, aryl, heteroaryl, cycloalkyl, heterocyclyl, arylalkyl, arylalkenyl, cycloalkylalkyl, heterocyclylalkyl, heteroarylalkyl, —CF$_3$, —OCF$_3$, —CN, —OR$^2$, —NR$^2$R$^3$, —C(O$_2$)R$^2$, —C(O)R$^2$, —C(O)NR$^2$R$^3$, —SO$_3$H, —SR$^2$, —S(O$_2$)R$^2$, —S(O$_2$)NR$^2$R$^3$, —N(R$^2$)S(O$_2$)R$^3$, —N(R$^2$)C(O)R$^3$, —N(R$^2$)C(O)NR$^2$R$^3$, —NO$_2$ and X-containing moieties through which a polyoxometalate molecule can be linked to one ore more other polyoxometalate molecules, each of R$^2$ and R$^3$ being independently selected from the group consisting of H, alkyl, aryl and cycloalkyl, q is the number of R ranging from 0 to 8 and y is the number of oxygen atoms ranging from 32 to 40.

17. The process according to claim 16, wherein the organic substrates are unsubstituted or substituted hydrocarbons such as branched or unbranched alkanes and alkenes having carbon numbers from C1 to C20, cycloalkanes, cycloalkenes, aromatic hydrocarbons or mixtures thereof.

18. The process according to claim 16, wherein the polyoxometalate is supported on a solid support.

19. The process according to claim 18, wherein the supported polyoxometalate is calcined at a temperature not exceeding the transformation temperature of the polyoxometalate.

20. A Process for oxidizing organic substrates comprising: contacting a first organic substrate with one or more polyoxometalates represented by the formula or solvates thereof, wherein A represents a cation, n is the number of the cations, m is the charge of the polyanion, M represents a transition metal selected from Pd, Pt, Au, Rh, Ir and mixtures thereof, X represents a heteroatom selected from As, Sb, Bi, P, Si, Ge, B, Al, Ga, S, Se, Te and mixtures thereof, R is a group covalently bound to X, provided X is P, As, Si or Ge, and is independently selected from the group consisting of H, alkyl, alkenyl, alkynyl, aryl, heteroaryl, cycloalkyl, heterocyclyl, arylalkyl, arylalkenyl, cycloalkylalkyl, heterocyclylalkyl and heteroarylalkyl, wherein each of said alkyl, alkenyl, alkynyl, aryl, heteroaryl, cycloalkyl and heterocyclyl can be unsubstituted or substituted with one or more groups which can be the same or different, each group being independently selected from the group consisting of halogen, alkyl, alkenyl, alkynyl, aryl, heteroaryl, cycloalkyl, heterocyclyl, arylalkyl, arylalkenyl, cycloalkylalkyl, heterocyclylalkyl, heteroarylalkyl, —CF$_3$, —OCF$_3$, —CN, —OR$^2$, —NR$^2$R$^3$, —C(O$_2$)R$^2$, —C(O)R$^2$, —C(O)NR$^2$R$^3$, —SO$_3$H, —SR$^2$, —S(O$_2$)R$^2$, —S(O$_2$)NR$^2$R$^3$, —N(R$^2$)S(O$_2$)R$^3$, —N(R$^2$)C(O)R$^3$, —N(R$^2$)C(O)NR$^2$R$^3$, —NO$_2$ and X-containing moieties through which a polyoxometalate molecule can be linked to one ore more other polyoxometalate molecules, each of R$^2$ and R$^3$ being independently selected from the group consisting of H, alkyl, aryl and cycloalkyl, q is the number of R ranging from 0 to 8 and y is the number of oxygen atoms ranging from 32 to 40;

(ii) recovering the polyoxometalates;

(iii) contacting the polyoxometalates with a solvent at a temperature of 50° C. or more to obtain a recycled polyoxometalate;

(iv) contacting the recycled polyoxometalate with a second organic substrate, which may be the same as or different from the first organic substrate; and (v) optionally repeating steps (ii) to (iv).

21. A mixed metal oxide catalyst prepared from a precursor comprising polyoxometalate represented by the formula or solvates thereof, wherein A represents a cation, n is the number of the cations, m is the charge of the polyanion, M represents a transition metal selected from Pd, Pt, Au, Rh, Ir and mixtures thereof, X represents a heteroatom selected from As, Sb, Bi, P, Si, Ge, B, Al, Ga, S, Se, Te and mixtures thereof,

R is a group covalently bound to X, provided X is P, As, Si or Ge, and is independently selected from the group consisting of H, alkyl, alkenyl, alkynyl, aryl, heteroaryl, cycloalkyl, heterocyclyl, arylalkyl, arylalkenyl, cycloalkylalkyl, heterocyclylalkyl and heteroarylalkyl, wherein each of said alkyl, alkenyl, alkynyl, aryl, heteroaryl, cycloalkyl and heterocyclyl can be unsubstituted or substituted with one or more groups which can be the same or different, each group being independently selected from the group consisting of halogen, alkyl, alkenyl, alkynyl, aryl, heteroaryl, cycloalkyl, heterocyclyl, arylalkyl, arylalkenyl, cycloalkylalkyl, heterocyclylalkyl, heteroarylalkyl, —CF$_3$, —OCF$_3$, —CN, —OR$^2$, —NR$^2$R$^3$, —C(O$_2$)R$^2$, —C(O)R$^2$, —C(O)NR$^2$R$^3$, —SO$_3$H, —SR$^2$, —S(O$_2$)R$^2$, —S(O$_2$)NR$^2$R$^3$, —N(R$^2$)S(O$_2$)R$^3$, —N(R$^2$)C(O)R$^3$, —N(R$^2$)C(O)NR$^2$R$^3$, —NO$_2$ and X-containing moieties through which a polyoxometalate molecule can be linked to one ore more other polyoxometalate molecules, each of R$^2$ and R$^3$ being independently selected from the group consisting of H, alkyl, aryl and cycloalkyl, q is the number of R ranging from 0 to 8 and y is the number of oxygen atoms ranging from 32 to 40.

22. The process according to claim 21, wherein the mixed metal oxide catalysts are Mitsubishi-type catalysts.

23. A nanocatalyst prepared from a precursor comprising polyoxometalate represented by the formula or solvates thereof, wherein A represents a cation, n is the number of the cations, m is the charge of the polyanion, M represents a transition metal selected from Pd, Pt, Au, Rh, Ir and mixtures thereof,

X represents a heteroatom selected from As, Sb, Bi, P, Si, Ge, B, Al, Ga, S, Se, Te and mixtures thereof, R is a group covalently bound to X, provided X is P, As, Si or Ge, and is independently selected from the group consisting of H, alkyl, alkenyl, alkynyl, aryl, heteroaryl, cycloalkyl, heterocyclyl, arylalkyl, arylalkenyl, cycloalkylalkyl, heterocyclylalkyl and heteroarylalkyl, wherein each of said alkyl, alkenyl, alkynyl, aryl, heteroaryl, cycloalkyl and heterocyclyl can be unsubstituted or substituted with one or more groups which can be the same or different, each group being independently selected from the group consisting of halogen, alkyl, alkenyl, alkynyl, aryl, heteroaryl, cycloalkyl, heterocyclyl, arylalkyl, arylalkenyl, cycloalkylalkyl, heterocyclylalkyl, heteroarylalkyl, —CF$_3$, —OCF$_3$, —CN, —OR$^2$, —NR$^2$R$^3$, —C(O$_2$)R$^2$, —C(O)R$^2$, —C(O)NR$^2$R$^3$, —SO$_3$H, —SR$^2$, —S(O$_2$)R$^2$, —S(O$_2$)NR$^2$R$^3$, —N(R$^2$)S(O$_2$)R$^3$, —N(R$^2$)C(O)R$^3$, —N(R$^2$)C(O)NR$^2$R$^3$, —NO$_2$ and X-containing moieties through which a polyoxometalate molecule can be linked to one ore more other polyoxometalate molecules, each of R$^2$ and R$^3$ being independently selected from the group consisting of H, alkyl, aryl and cycloalkyl, q is the number of R ranging from 0 to 8 and y is the number of oxygen atoms ranging from 32 to 40, wherein the nanocatalyst is obtained by reduction of the polyoxometalate.

24. A polyoxometalate represented by the formula or solvates thereof, wherein

A represents a cation, n is the number of the cations, m is the charge of the polyanion,

R is a group covalently bound to X and is independently selected from the group consisting of H, alkyl, alkenyl, alkynyl, aryl, heteroaryl, cycloalkyl, heterocyclyl, arylalkyl, arylalkenyl, cycloalkylalkyl, heterocyclylalkyl and heteroarylalkyl, wherein each of said alkyl, alkenyl, alkynyl, aryl, heteroaryl, cycloalkyl and heterocyclyl can be unsubstituted or substituted with one or more groups which can be the same or different, each group being independently selected from the group consisting of halogen, alkyl, alkenyl, alkynyl, aryl, heteroaryl, cycloalkyl, heterocyclyl, arylalkyl, arylalkenyl, cycloalkylalkyl, heterocyclylalkyl, heteroarylalkyl, —CF$_3$, —OCF$_3$, —CN, —OR$^2$, —NR$^2$R$^3$, —C(O$_2$)R$^2$, —C(O)R$^2$, —C(O)NR$^2$R$^3$, —SO$_3$H, —SR$^2$, —S(O$_2$)R$^2$, —S(O$_2$)NR$^2$R$^3$, —N(R$^2$)S(O$_2$)R$^3$, —N(R$^2$)C(O)R$^3$, —N(R$^2$)C(O)NR$^2$R$^3$, —NO$_2$ and X-containing moieties through which a polyoxometalate molecule can be linked to one ore more other polyoxometalate molecules, each of R$^2$ and R$^3$ being independently selected from the group consisting of H, alkyl, aryl and cycloalkyl, q is the number of R ranging from 0 to 8 and y is the number of oxygen atoms ranging from 32 to 40.

25. A polyoxometalate represented by the formula or solvates thereof, wherein

A represents a cation, n is the number of the cations, m is the charge of the polyanion.

26. A polyoxometalate represented by the formula or solvates thereof, wherein
A represents a cation,
n is the number of the cations,
m is the charge of the polyanion.

27. A polyoxometalate represented by the formula:

$(A_n)^{m+}[M_{13}X_8O_{40}]^{m-}$, wherein
A represents a cation,
n is the number of the cations,
m is the charge of the polyanion,
M represents a transition metal selected from Pd, Pt, Au, Rh, Ir and mixtures thereof, and
X represents a heteroatom selected from $As^V$, $Sb^V$, $Bi^V$, $P^V$ and mixtures thereof.

28. A polyoxometalate represented by the formula:

$[M_{13}O_{32}(XR)_8]^{m-}$ wherein M represents a transition metal selected from Pd, Pt, Au, Rh, Ir and mixtures thereof, X is $P^V$, $As^V$, $Si^{IV}$ and/or $Ge^{IV}$ and R is —H, —$C_6H_5$, —$CH_3$, —$C_2H_5$, —$CH_2COOH$ or —$CH_2NH_2$.

29. The polyoxometalate of claim 24, wherein A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

30. The polyoxometalate of claim 24, wherein A is selected from the group consisting of hydrogen, sodium, and combinations thereof.

31. The polyoxometalate of claim 25, wherein A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

32. The polyoxometalate of claim 25, wherein A is selected from the group consisting of hydrogen, sodium, and combinations thereof.

33. The polyoxometalate of claim 26, wherein A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

34. The polyoxometalate of claim 26, wherein A is selected from the group consisting of hydrogen, sodium, and combinations thereof.

35. The polyoxometalate of claim 27, wherein A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

36. The polyoxometalate of claim 27, wherein A is selected from the group consisting of hydrogen, sodium, and combinations thereof.

37. The polyoxometalate of claim 28, wherein A is selected from the group consisting of hydrogen, lithium, sodium, potassium, rubidium, cesium, magnesium, calcium, strontium, barium, titanium, vanadium, chromium, lanthanum, lanthanide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

38. The polyoxometalate of claim 28, wherein A is selected from the group consisting of hydrogen, sodium, and combinations thereof.

* * * * *